United States Patent [19]
Kablik

[11] Patent Number: 5,261,895
[45] Date of Patent: Nov. 16, 1993

[54] APPARATUS FOR GUIDING SURGICAL INSTRUMENTS INTO A SURGICAL SITE AND BLOCKING ESCAPE OF FLUIDS FROM THE SITE

[75] Inventor: Joseph J. Kablik, Los Gatos, Calif.

[73] Assignee: Stryker Corporation, Kalamazoo, Mich.

[21] Appl. No.: 766,803

[22] Filed: Sep. 26, 1991

[51] Int. Cl.$^5$ .............................................. A61M 5/00
[52] U.S. Cl. ................................ 604/249; 604/167; 604/246; 604/256
[58] Field of Search .............. 604/27, 30, 33, 164-169, 604/246, 249, 247, 256, 283-284, 248; 137/329.1-329.3, 901; 251/149.6-149.7

[56] References Cited
U.S. PATENT DOCUMENTS

| | | | |
|---|---|---|---|
| 1,034,995 | 8/1912 | Gannon | 137/901 |
| 1,103,967 | 7/1914 | Hughes | 604/249 |
| 3,570,484 | 3/1971 | Steer | 604/249 |
| 3,739,778 | 6/1973 | Monestere, Jr. et al. | 604/167 |
| 3,895,632 | 7/1975 | Plowiecki | 604/169 |
| 4,233,982 | 11/1980 | Bauer et al. | 604/169 |
| 4,245,635 | 1/1981 | Kontos . | |
| 4,261,357 | 4/1981 | Kontos . | |
| 4,510,933 | 4/1985 | Wendt et al. | 604/167 |
| 4,535,773 | 8/1985 | Yoon | 604/169 |
| 4,585,435 | 4/1986 | Vaillancourt | 604/27 |
| 4,601,710 | 7/1986 | Moll | 604/165 |
| 4,931,042 | 6/1990 | Holmes et al. . | |
| 4,943,280 | 7/1990 | Lander . | |
| 4,998,919 | 3/1991 | Schnepp-Pesch et al. | 604/164 |
| 5,006,114 | 4/1991 | Rogers et al. | 604/167 |
| 5,030,206 | 7/1991 | Lander | 604/164 |
| 5,131,249 | 7/1992 | Nixon | 137/329.3 |

FOREIGN PATENT DOCUMENTS

| | | |
|---|---|---|
| 1267377 | 3/1968 | Fed. Rep. of Germany . |
| 3048203 | 7/1982 | Fed. Rep. of Germany ........ 604/51 |
| 2267801 | 11/1975 | France ............................ 604/249 |

OTHER PUBLICATIONS

Exhibit A, prior art figure, as discussed in specification.

*Primary Examiner*—C. Fred Rosenbaum
*Assistant Examiner*—Mark Bockelman
*Attorney, Agent, or Firm*—Flynn, Thiel, Boutell & Tanis

[57] ABSTRACT

Apparatus for guiding insertion of surgical instruments into a surgical site while blocking escape of fluids, including gas under pressure, therethrough from the surgical site. A generally Y-shaped housing comprises an elongate instrument guide having a distal end insertable in the surgical site and an elongate instrument passage through which elongate instruments are insertable into the surgical site. A valve seat is provided in the instrument passage. A valve member is movable into contact with the valve seat for blocking escape of fluid from the surgical site therepast along the instrument passage when no instrument occupies such instrument passage. Such housing includes a tubular valve guide having an elongate valve passage intersecting the instrument passage and along which the valve member is movable toward and away from the valve seat. The valve member is urged resiliently along the valve passage toward the valve seat for closing the instrument passage when no surgical instrument is in the instrument passage and for resiliently allowing a surgical instrument inserted into the instrument passage to push aside the valve member, back into the valve passage, to allow continued insertion of the surgical instrument past the valve member into the surgical site.

4 Claims, 4 Drawing Sheets

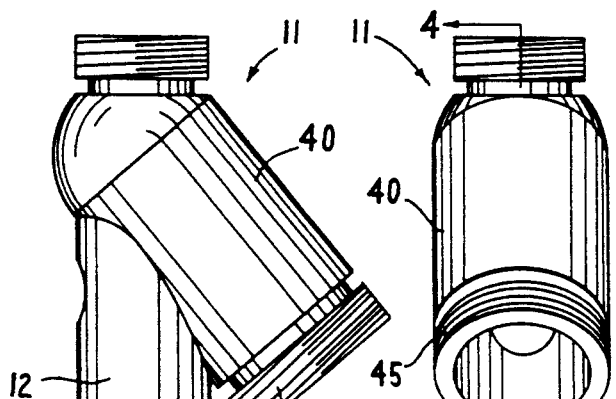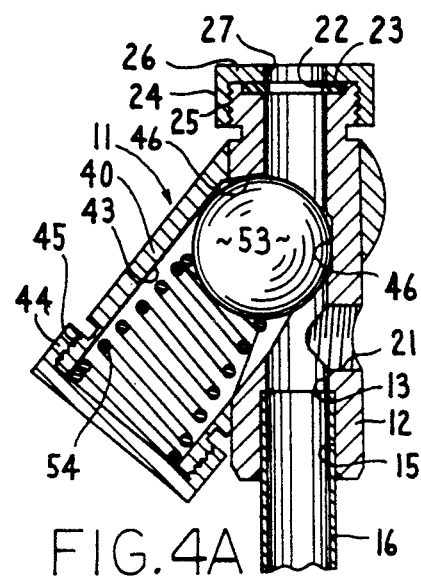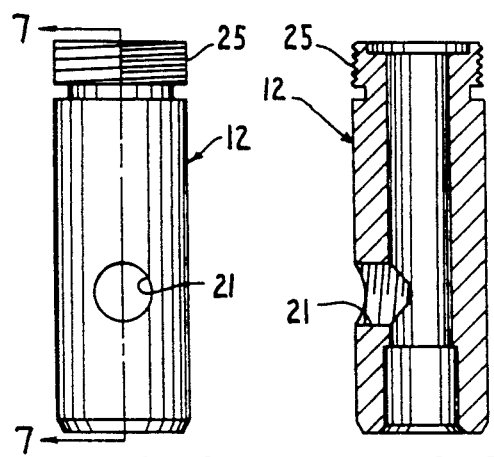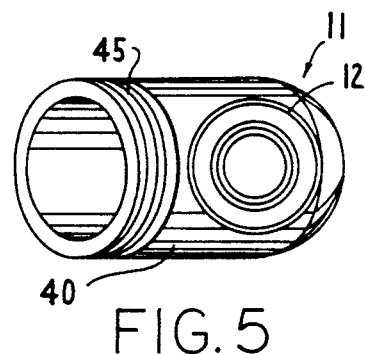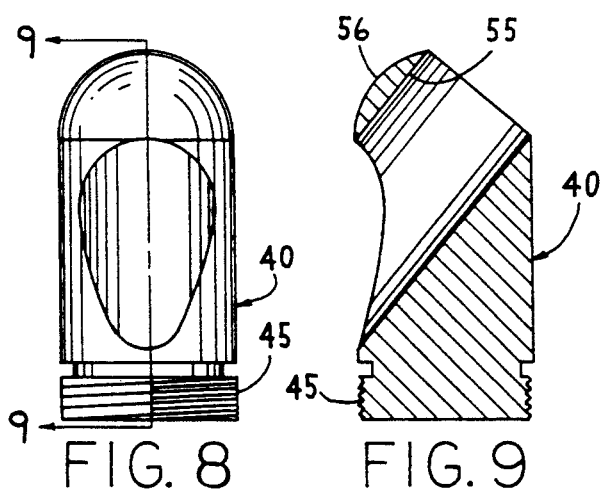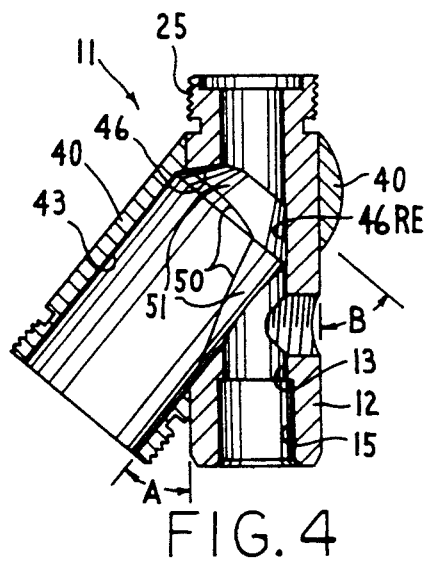

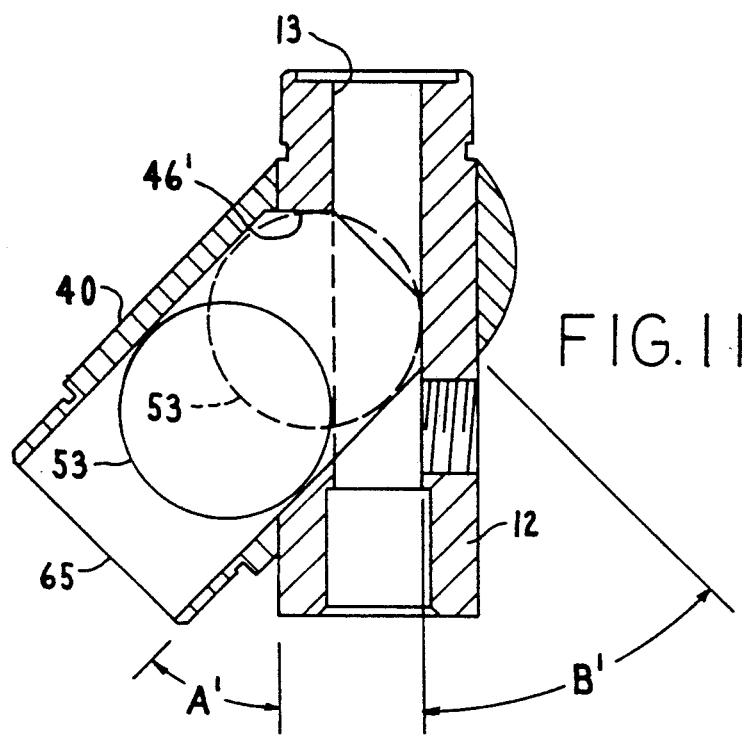
FIG. 11
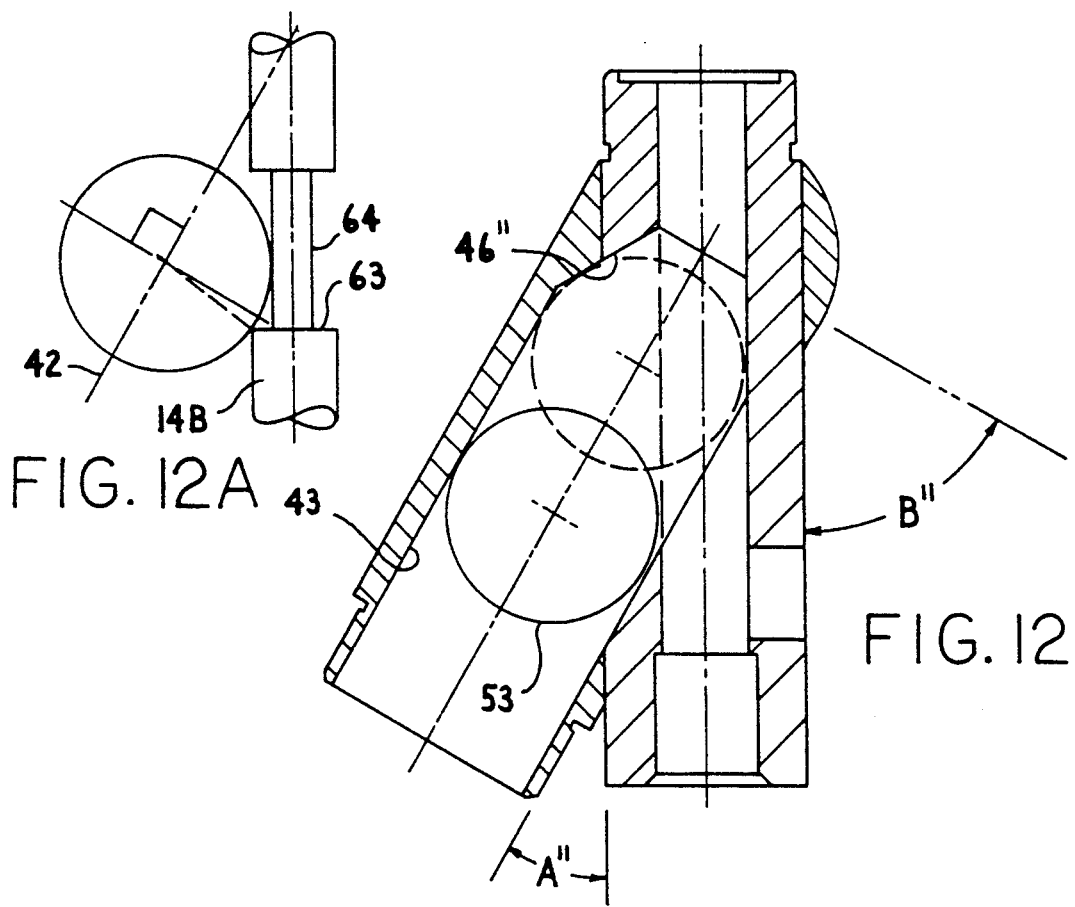
FIG. 12A
FIG. 12

5,261,895

APPARATUS FOR GUIDING SURGICAL INSTRUMENTS INTO A SURGICAL SITE AND BLOCKING ESCAPE OF FLUIDS FROM THE SITE

FIELD OF THE INVENTION

This invention relates to apparatus for telescopingly guiding a series of surgical instruments into a surgical site and blocking unintended loss of fluid pressure from the surgical site.

BACKGROUND OF THE INVENTION

It is known to enter the end of an instrument guide (e.g. trocar tube) into a surgical site, and telescopically guide through the instrument guide various elongate surgical instruments into the surgical site. In one example, a sharply pointed piercing instrument of elongate dimension (e.g. a trocar) is inserted telescopically through an instrument guide. The point of the trocar is then used to make an incision in the patient at the surgical site and the adjacent end of the instrument guide is inserted into the incision. The trocar is then withdrawn from the instrument guide and set aside. Thereafter, a desired sequence of surgical instruments can be inserted telescopically through the instrument guide into the surgical site. Techniques of this known type are used in a variety of surgical procedures, for example, on a larger scale, laparoscopy or, on a smaller scale, arthroscopic joint surgery, such as arthroscopic knee surgery.

Such elongate surgical instruments insertable through such an instrument guide include instruments allowing the surgeon vision into the surgical site, which may be provided with a leading tip of transparent material such as glass or clear plastic and which may include lighting, direct vision and/or camera means.

Such elongate surgical instruments also include a variety of cutting or other tissue modifying instruments. The latter may have surface irregularities near the distal working tip, e.g. grooves, etc.

It is known to inject gas under pressure into the surgical site, through the instrument guide, or otherwise, to enlarge the surgical cavity, e.g. to allow the surgeon better vision of the tissue to be surgically treated or modified or to allow the surgeon more room in which to manipulate instruments to carry out the surgical procedure. To avoid loss of pressure gas from the surgical site through the instrument guide, the latter typically has a resilient annular seal remote from the surgical site and which sealingly surrounds the surgical instrument.

The prior art has made several attempts to block loss of pressure gas from the surgical site with no surgical instrument in the instrument guide.

For example, it has been known to provide a so-called trumpet valve on the instrument guide between the surgical site and the annular resilient seal. More particularly, the trumpet valve comprises a cylindrical valve core movable in a cylindrical passage communicating at right angles with the longitudinal passage of the instrument guide. A spring urges the cylindrical valve core axially in one direction to close the longitudinal passage in the instrument guide. An external push button can be pushed by the surgeon to displace the cylindrical valve core so that the longitudinal passage in the instrument guide registers coaxially with a diametral hole in the valve core of identical diameter so that an elongate surgical instrument can be telescopically inserted through and withdrawn from the instrument guide. However, while generally satisfactory, Applicant has found that such a trumpet valve construction has disadvantages. For example, it requires an extra hand to operate the trumpet valve push button, hold the instrument guide in place, and remove or insert a surgical instrument. Further, such a trumpet valve construction requires excessively tight tolerances in manufacturing to perform properly in the field, is expensive to manufacture, and can involve difficulties in disassembly for sterilization purposes and reassembly thereafter.

Another prior art apparatus has instead utilized a trap door valve, in the form of a plate-like valve member which is hinged and spring biassed to swing against an annular valve seat enclosed in a radially enlarged chamber intermediate the ends of the instrument guide. One such prior trap door valve utilizes a trap door with a convex ball-shaped face opposing the seat. A coiled torsion spring is wound around a fixed pin skewed with respect to the instrument passage axis and has one end extending lever-like and fixedly supporting the ball-faced member, to act both as a pivot hinge and a resilient biassing element. The annular valve seat is coaxial with the instrument passage and the center of the ball-like movable valve member lies on the instrument passage axis in its closed position. Applicant has noted disadvantages with prior apparatus of this kind. For example, the initial incision in the surgical site is to be made by a sharp, pointed obturator and it is critical that the point of the obturator be maintained sharp up to the time it reaches the skin of the patient and makes the incision thereof. However, to open trap door valves of the above-mentioned kind, the sharp point of the obturator must push against the movable trap door valve member and swing it out of the way so that the obturator can proceed therepast and into the surgical site. If the opposed trap door face is of relatively soft material, the sharp point of the obturator will tend either to dig into and fail to open the trap door member or to damage the surface thereof against future use. On the other hand, if the opposed trap door face is of relatively hard material, the latter may blunt or dull the point of the obturator as such point skids along the trap door face in the process of pushing it out of the way. Moreover, successive surgical instruments passing through the instrument guide to the surgical site or being pulled out of the surgical site must also push open the trap door member. Instruments having a transparent or otherwise delicate distal tip could be damaged by scuffing along the surface of the trap door valve member in the process of opening it. Moreover, irregularly shaped instrument distal portions, for example some cutting or other tissue modifying heads, may also tend to snag on the opposed trap door face as they attempt to push it aside to reach the surgical site, or may snag on the free edge of the trap door valve member while attempting to withdraw outward past it.

Another prior art apparatus is known in which an instrument guide is sealed by means of a rubber, washer-like member with a hole cut not quite all the way therethrough. The valve member is mounted on top of the instrument guide in the same manner as a washer and when an instrument is inserted into the instrument guide it breaks through the thinnest part of the washer material and pushes aside adjacent parts of the washer material in the manner of a flap or flaps opening, such that the instrument can be inserted through the instrument guide. This type of valve is used for simple instrument guide designs and is useful for inexpensive disposable devices. However, the valve does not provide an airtight seal when the instrument is withdrawn from the instrument guide.

Accordingly, it is an object of the present invention to overcome certain difficulties in prior art apparatus of this general kind.

Other objects and purposes of the present invention will be apparent to persons acquainted with apparatus of this general type upon reading the following description and inspecting the accompanying drawings.

One aspect of the invention includes apparatus for guiding insertion of surgical instruments into a surgical site while blocking escape of fluids, such as gas under pressure, therethrough from the surgical site. Such apparatus comprises elongate instrument and valve passages intersecting at an acute angle with a valve seat adjacent their intersection and a valve member movable along the valve passage toward the valve seat for blocking fluid escape from the surgical site when no instrument is in the instrument passage and alternatively for being moved away from the valve seat by insertion of an instrument through the instrument passage, for allowing entry of an instrument to the surgical site.

BRIEF DESCRIPTION OF THE DRAWINGS

FIG. 2 is an enlarged side elevational view of the housing of the FIG. 1 apparatus.

FIG. 3 is a side view (taken from the right side of FIG. 2) of the FIG. 2 housing.

FIG. 4 is a central cross-sectional view substantially taken on the line 4—4 of FIG. 3.

FIG. 4A is a central cross-sectional view of the FIG. 1 apparatus, substantially as taken on the line 4—4 of FIG. 3, and without an instrument therein.

FIG. 5 is a bottom view of the FIG. 4 housing.

FIG. 6 is an elevational view of the instrument guide of the FIG. 2 housing.

FIG. 7 is a central cross-sectional view substantially taken on the line 7—7 of FIG. 6.

FIG. 8 is an elevational view of the ball guide of the FIG. 2 housing prior to machining of a ball passage therein.

FIG. 9 is a sectional view substantially taken on the line 9—9 of FIG. 8.

FIG. 10D is similar to FIG. 10A but shows an irregularly shaped instrument periphery.

FIG. 11 is a view similar to FIG. 10 but fragmentary and showing a modification with a larger included angle between the ball passage and instrument passage axes.

FIG. 12 is a view similar to FIG. 10 but fragmentary and showing a modification with a smaller included angle between the axes of the ball passage and instrument passage.

FIG. 12A is similar to FIG. 10D, but relates to the FIG. 12 modification.

DETAILED DESCRIPTION

Figure 1:
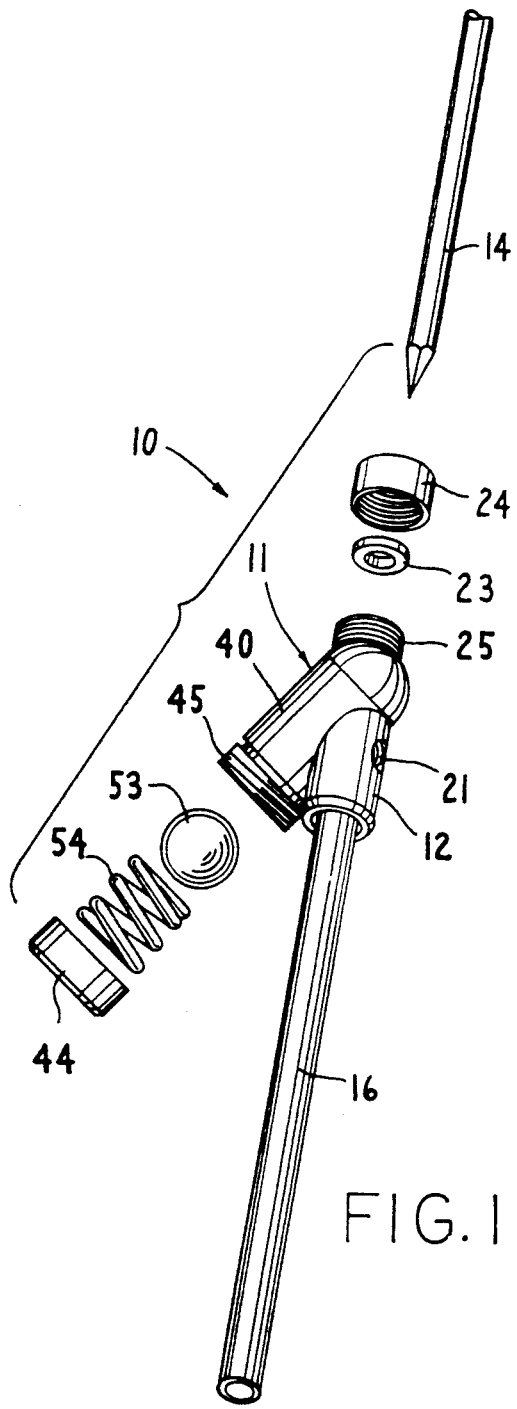
FIG. 1 is an exploded pictorial view of an apparatus embodying the invention and fragmentarily showing an obturator usable therewith.

Turning to FIG. 1, an apparatus 10 embodying the invention comprises a substantially Y-shaped housing 11. The housing includes an elongate tubular instrument guide 12. The instrument guide 12 has an elongate instrument passage 13 (FIG. 4) extending longitudinally therethrough. The instrument passage 13 is sized to receive snugly but slidably therethrough one or more elongate surgical instruments, examples of which are shown at 14, 14A and 14B in FIGS. 1, 1A and 1B, respectively.

The diameter of the bottom portion of the instrument passage 13 in the instrument guide 12 is formed as an enlarged diameter, substantially cylindrical, downward opening recess 15. A tube extension 16 (FIG. 10) has its upper end fixed in the downward facing recess 15 of the instrument guide 12 to downwardly (in FIG. 10) continue the instrument passage 13 in a flush coaxial manner. Thus, in the embodiment shown, the interior wall of the instrument passage 13 in the instrument guide 12 has an internal diameter equal to that of the continued instrument passage 13 in the instrument guide 12. This allows a given instrument (the instrument 14 being shown in FIG. 10 by way of example) to slide unhindered, back and forth, between the extension tube 16 and the instrument guide 12. The extension tube 16 can be fixed in the recess 15 of the instrument guide 12 by any convenient means, such as by a press fit, a threaded connection or in any other convenient manner.

Figure 10:
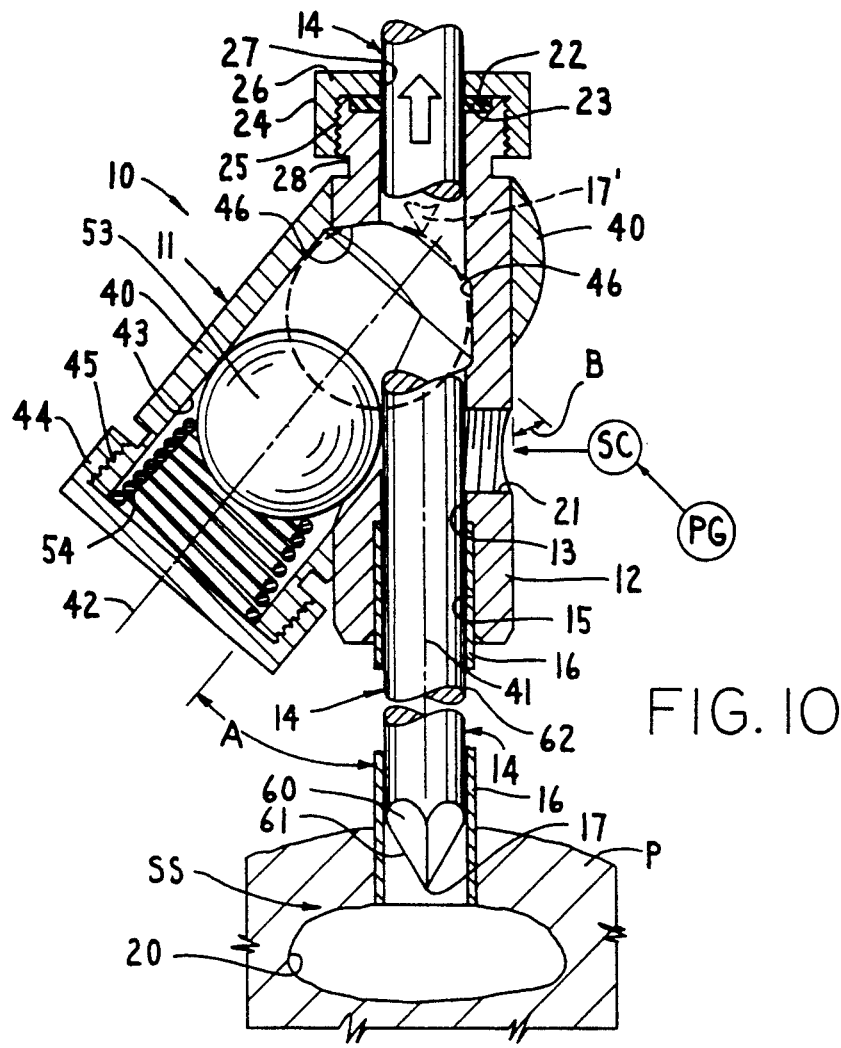
FIG. 10 is a central cross-sectional view similar to FIG. 4A but enlarged, and with an instrument installed therethrough.

For purposes of illustration of the use of the apparatus, FIG. 10 rather diagrammatically shows the bottom of extension tube 16 having entered the tissue of a patient P following making of an incision I by the pointed end 17 of the pointed incision-making instrument 14 (e.g. obturator or a trocar member). Thus, as seen in FIG. 10, the bottom of the extension tube 16 is entered into the surgical site SS and the obturator 14 is being withdrawn upwardly.

Figures 1A, 1B:
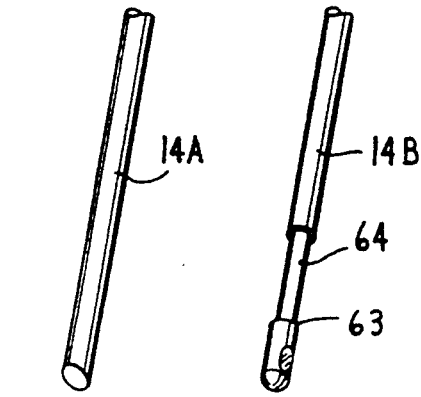
FIG. 1A is a fragmentary, schematic, pictorial view of an optical type of surgical instrument usable with the FIG. 1 apparatus.
FIG. 1B is a fragmentary, schematic, pictorial view of a further type of surgical instrument usable with the apparatus of FIG. 1 and having an irregularly shaped distal portion.

It may be desired to inject into the surgical site SS a quantity of inert gas under pressure to expand the opening in the patient's tissue at the surgical site SS to form a cavity schematically shown at 20, to give the surgeon more room in which to carry out the desired surgical procedures at the surgical site, to facilitate inspection by optical surgical instrumentation, such as that at 14A in FIG. 1A, or the like. To this end, the instrument guide 12 may be provided with a port 21 for connection of the instrument passage 13 through a conventional, manually operable, on/off valve, such as a stopcock, schematically indicated at SC, for receiving pressurized gas from a pressurized gas source, here schematically indicated at PG. The stopcock SC can be sealingly fixed in the port 21 by any convenient means, such as by a threaded connection.

The upper end of the instrument passage 13 communicates upward through an enlarged diameter, substantially cylindrical recess 22 (FIG. 10). The recess 22 receives a resilient sealing ring 23 which snugly and sealingly, but slidably, engages the periphery of an instrument 14 so as to block the escape of gas therepast outwardly from the cavity 20 of the surgical site SS. An annular cap 24 threads at 25 telescopically over the upper (FIG. 10) end of the instrument guide 12 and has an annular top 26 that blocks upward escape of the seal ring 23 from the recess 22. The top 26 of the cap 24 has a central opening 27, of diameter similar to the diameter of the instrument passage 13 of the instrument guide 12, for loosely slidably receiving an instrument 14 longitudinally therethrough. In the embodiment shown, the periphery of the instrument guide 12 is provided with a thread relief groove 28 below the threads 25 and cap 24. The cap 24 and seal ring 23 are removable from the instrument guide 12 for sterilization and, if needed, replacement of the seal ring 23.

To the extent above described, the apparatus 10 is similar to a prior art device manufactured by the assignee of the present invention.

Turning now to aspects of the disclosed apparatus more specifically involving the present invention, the housing 11 further includes a tubular guide 40 (FIG. 10). The central length axes 41 and 42 of the instrument guide 12 and guide 40 are coplanar. The tubular guide 40 is fixed at an acute angle A, facing toward the surgical site SS, to the instrument guide 12. As hereafter discussed, it is generally satisfactory that the angle A lie between 30° to 45°, although it is preferred that the angle A be about 40°.

The tubular guide 40 has a central, cylindrical passage 43 opening through its free (bottom in FIG. 10) end, namely the end closest to the surgical site SS. A cup-shaped cap 44 threaded at 45 on the outside of the free end of the tubular guide 40 to close the bottom end of the cylindrical passage 43.

At its upper end, the cylindrical passage 43 (FIG. 4) opens to the instrument passage 13 of the instrument guide 12 through a frustoconical valve seat 46. The frustoconical valve seat 46 preferably lies all within the instrument passage 13 of the instrument guide 12. Thus, the frustoconical valve seat 46 forms a relief in the otherwise preferably cylindrical instrument passage 13. An angle B subtended by a diametral plane of the cylindrical passage 43 (and of the frustoconical valve seat 46), on the one hand, and the central axis 41 (and wall) of the instrument passage 13 preferably is complementary to the angle A. More particularly, angles A and B preferably total 90°. This is desirable because, as seen in FIG. 4, it allows the rightwardmost element 46RE of the frustoconical valve seat 46 to coincide with the rightwardmost element of the instrument passage 13, or to be parallel to and slightly recessed into the peripheral wall of the instrument passage 13 at its right side. The term "element" is used immediately above in the sense of the plurality of parallel line elements which geometrically define any cylindrical surface and in the sense of the plurality of convergent line elements which geometrically define any conical surface. In other words, the rightwardmost (FIG. 4) side of the frustoconical valve seat 46 is preferably slightly indented in the rightwardmost side of the instrument passage 13. Manufacturing tolerances permit the frustoconical valve seat 46 to slightly indent the right side of the instrument passage 13 but preferably not by more than a few thousandths of an inch (for example, eight thousandths of an inch).

Because of the convergence of the central axes 41 and 42 of the instrument passage 13 and cylindrical passage 43 (i.e. of the instrument guide 12 and tubular guide 40), the frustoconical valve seat 46 and adjacent portion of the coaxial cylindrical passage 43 penetrate through the sidewall of the instrument guide 12 as shown at 50 in FIG. 4 and expose the material of the instrument guide 12 as shown at 51 in FIG. 4.

Snugly, but slidably and rollably, disposed within the cylindrical passage 43, for sealing engagement with the frustoconical valve seat 46, is a valve ball 53 (FIGS. 4A and 10). The ball 53 is lightly urged by a coil compression spring 54 toward the valve seat 46. The spring 54 is backed by the cap 44. The spring force is low, preferably less than two pounds, and just enough to reliably seat the ball 53 and seal the seat 46 when no instrument is in the instrument passage 13.

The spherical diameter of the ball 53 exceeds the diameter of the instrument passage 13 by a substantial margin, here by a multiplier of about 2 to 2½. In one unit constructed according to the invention, the diameter of the instrument passage 13 was 0.222 inch and the diameter of the ball was 0.500 inch, with the cylindrical passage 43 being of 0.510 inch diameter.

The instrument guide 12, ball housing 40, ball 53 and spring 54 are preferably of stainless steel, although it is contemplated that suitable plastics materials can be substituted for stainless steel in one or more of the above-named elements.

OPERATION

The operation of the apparatus 10 has been generally indicated above but will be briefly reviewed for convenient reference below.

In FIG. 10, with the valve ball 53 in its dotted line position shown, use of the apparatus in a surgical procedure can begin with downward insertion into the instrument passage 13 of a suitable incision-making instrument, such as a sharply pointed piercing instrument, here the trocar 14. The pointed tip 17 of the trocar 14 passes the sealing ring 23 and then contacts the rightward sloping surface of the ball 53 in its dotted line, closed (valve seat closing) position shown in dotted lines in FIG. 10 and solid lines in FIG. 10A. At the point of initial contact, the slope of the trocar pointed end 17 is at a relatively small angle TA (FIG. 10A) to the tangent plane TP of the ball 53 at the point of contact. Accordingly, the pointed end 17 of the trocar 14 does not tend to dig into the surface of the ball 53 even if the ball is of a relatively soft material, and does not tend to dull itself on the surface of the ball 53 even if the ball is of material as hard or harder than the pointed end 17 of the trocar 14. Instead, the sloping flank 60 or edge 61 of the pointed trocar end 17 tends to shoulder aside, in a leftward and downward direction, the ball 53.

Figure 10A:
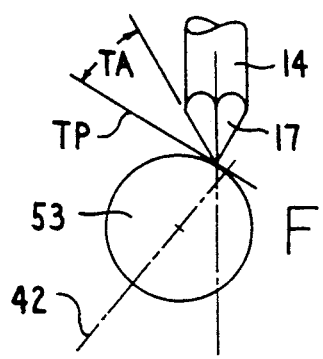
FIGS. 10A and 10B are diagrams showing successive positions of insertion of an obturator tip past the ball of the FIG. 10 apparatus.

In the FIG. 10A embodiment, the pointed end 17 of the trocar 14 initially contacts the ball 53 almost on the central axis 42 of the tubular ball guide 40 such that the force of the trocar point 17 against the ball is virtually along that centerline. More particularly, a force applied to a point on the hardened surface of a ball has a component acting to push the ball in a direction along the radius of the ball through the point of contact. Accordingly, upon contact by the downward advancing tip 17 of the trocar 14, the ball easily is pushed downward and leftward into the bottom portion of the ball guide, with the only significant resistance being the relatively light backing force of the compression spring 54.

Figure 10C:
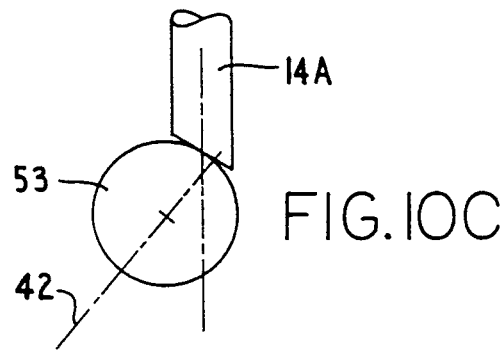
FIG. 10D is similar to FIG. 10A but shows an irreg- instrument tip.
Figure 10B:
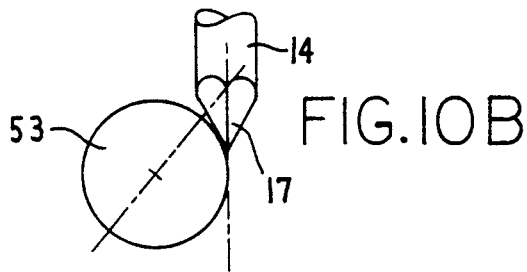

As the flank 60 or edge 61 of the pointed end 17 of the trocar 14 moves downwardly along the surface of the ball 53, as in FIG. 10B, if there is any significant friction with the surface of the ball 53, the ball 53 can easily rotate in response thereto. The ball is free to rotate within the ball guide 40 due to its generous clearance fit within the cylindrical passage 43 and the relatively light contact pressure of the backing spring 54.

It will thus be seen that there is no significant tendency of the trocar point 17, even when very sharp, to damage either itself or the ball 53 as it shoulders the ball aside.

After the trocar lower tip 17 has advanced downward past the ball, the following periphery 62 of the instrument 14 advances downward through the now open valve seat 46 and continues to press the ball 53 aside so that the ball tends to ride lightly against the periphery 62 of the tool 14 and be held lightly thereby in its retracted solid line position of FIG. 10.

Once the instrument point 17 has passed down through the surface tissue of the patient P to the desired depth, i.e. to the surgical site SS, the apparatus 10, and more particularly the bottom portion of the extension tube 16 can be pressed down into the incision to the depth of the surgical site SS, as shown in FIG. 10 in a schematic manner. The trocar 14 can then be withdrawn from the apparatus 10 by simply lifting it upward out of the instrument passage 13. The relatively light upward pressure of the backing spring 14 keeps the ball 53 riding lightly against the surface 62 of the trocar 14 as it is being withdrawn. Eventual movement of the pointed lower end 17 of the trocar 14 upward past the ball 53 enables the spring 54 to return the ball upward and rightward to close the valve seat 46, substantially in a reversal of the above-described insertion steps.

Thereafter, other instruments may be similarly inserted downward through the instrument passage 13. The bottom ends of these instruments will vary in shape from each other and from the trocar 14. See for example the optical instrument 14A of FIGS. 1A and 10C. In each instance, however, the bottom tip of the instrument will encounter the surface o the ball at a location spaced to the right of the ball center and at a location on the ball surface that faces directly away from the ball guide 40 and is located on or close adjacent the central axis 42 of the ball guide 40 so that, as in the case of the trocar 14, these other instruments tend to very lightly and easily shoulder aside the ball 53 as they advance downward toward the surgical site SS.

Figure 10D:
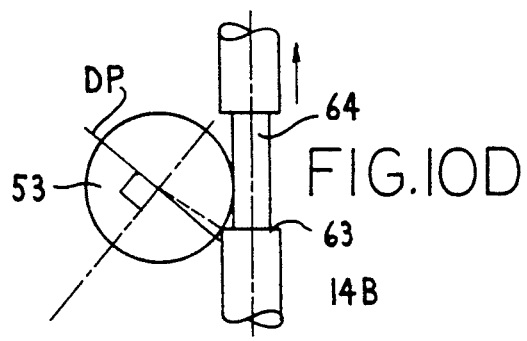

One or more instruments to be used in the surgical procedure may have irregularities in their peripheral surface near the working bottom end thereof. One rather extreme example is shown at 14B in FIG. 1B and 10D as having an elongate annular groove 64, which results in an upfacing annular step 63 (FIG. 1B). As the tool 14B (FIG. 10D) is pulled upward out of the surgical site, the groove 64 allows the ball 53 to advance upward and rightward a short distance out of its fully retracted solid line position of FIG. 10. The upfacing step 63 then encounters the ball. However, the angle A between the axes of the ball guide 40 and the instrument guide 12 is sufficiently large that the first contact of the shoulder 63 and the surface of the ball 53 occurs at a point above a diametral plane DP of the ball (namely a diametral plane perpendicular to the central axis 42 of the ball guide 40). Accordingly, as the instrument 14B is upward pulled, its shoulder 63 will shoulder the ball downwardly against the spring 54 rather than upwardly toward the seat 46. In other words, the up rising step 63 will shoulder the ball 53 back into its fully retracted solid line position of FIG. 10 rather than forcing it upward and immovably jamming the ball 53 and instrument 14B.

Further, with the angle A at about 40° as shown in FIG. 10, very little of the upper rightward end of the backing spring 54 leaves the confinement of the ball guide 40 and is exposed to the instrument passage 13 in the instrument guide 12, even with the ball 53 closing the valve seat 46. Hence, there is no tendency whatsoever for the spring to become entangled at its upper end or otherwise resist opening movement of the ball off the valve seat 46 or have any contact with an instrument being inserted or retracted from the instrument guide 12.

Moreover, with the angle A at about 40° (FIG. 10), the frustoconical valve seat 46 continues unbroken through its entire perimeter with the ball guide 40. More particularly, the uppermost element of the frustoconical valve seat 46 engages the fully seated ball 53 at a point spaced well to the left of the open instrument passage 13 so that the circle of contact of the seated ball with the seat is circumferentially complete. Thus, even if the seat is accidentally bored too deep into the instrument guide 12, the accidental upward and rightward misplacement of the valve seat 46 would have to be very large (e.g. about 0.030 inch), and therefore easily preventable, before the circular line of contact between the upper part of the seat and the seated ball moves inboard (rightward) into the instrument passage 13 and so creates a gap (and hence gas leak) between the seated ball and the upper part of the seat peripheral wall of the instrument guide 12.

MODIFICATIONS

However, substantial alterations of the angle A from the preferred 40° or so angle in FIG. 10 can eliminate some of the advantages of the FIG. 10 apparatus.

For example, referring to the modified FIG. 11 embodiment, same widens the angle A' to 45° and reduces the angle B' to 45° to maintain the total of angle A' and angle B' to 90°. In this modification, the circle of contact between the valve seat 46' and the ball 53 resting thereon is at the topmost element of the valve seat 46', nearly at the interior wall of the instrument passage 13. In this instance, if the valve seat 46 is bored just two thousandths of an inch beyond its intended position shown in FIG. 11, the circle of contact between ball and valve seat will be broken at the top of the valve seat and a leak will be created. When advancing a frustoconical milling cutter to form the valve seat 46', the depth of the seat 46' is measured from the leftward bottom end 65 of guide 40 which, due to stacking of tolerances in forming and assembling the instrument guide 12 and guide 40, a two thousandths inch depth error limit cannot reliably be met. In other words, during a production run, in some FIG. 11 modified devices, the valve seat 46' will be cut too deep into the instrument guide 12 so that the circle of contact between the ball and the seat will be broken at the top of the seat and leakage past the ball can thereby occur. In contrast to the few thousandths inch error margin in the FIG. 11 modification, in the preferred FIG. 10 embodiment, an overdepth of up to 30 thousandths of an inch can occur in the milling of the valve seat 46 without loss of continuity in the circular contact between the ball and valve seat.

A further modification is shown in FIG. 12 in which the angle A" is reduced to 30° and the seat angle B" is correspondingly increased to 60° to maintain a combined total of 90° as before.

As the included angle A" is narrowed to 30° as shown in FIGS. 12 and 12A, the resulting valve seat 46" approaches being too narrow to seat the ball 53 properly. Further, an instrument with an irregular peripheral shape, such as the instrument 14B with its upfacing step 63, may be unable to easily reliably shoulder the ball leftward and downwardly against its spring 54. The ability of the retracting (upward rising) instrument 14B to shoulder the ball leftward and downward depends on an interplay of factors, such as the depth of the annular groove 64 (how far into the instrument passage 13 it allows the ball to protrude), the angle of the shoulder 63 (radial to the instrument length axis or sloped upwardly or downwardly) and the amount of friction between the ball and the surfaces that it contacts. Here the radial step 63 engages the ball below a ball passage diametral plane through the center of the ball, and there may be a tendency for the ball to be pushed upward toward the valve seat 46' rather than downwardly away from it and, as a result, a tendency of the instrument 14B to jam in the instrument passage 13 during upward withdrawal therefrom. Even with the extremely disadvantageous configuration of the instrument 14B shown in FIG. 12A, any such tendency to jam is reduced as the angle A" increases and is essentially absent when the FIG. 10 preferred angle A of 40° or so is adopted. On the other hand, if the angle A" is narrowed past 30°, the possibility of such jamming as the instrument is being withdrawn tends to increase, even if the peripheral surface of the instrument is cylindrical and unbroken, where the ball has some friction in its contact with the instrument and with the interior surface of the ball guide passage 43.

A related problem with the FIG. 12 modification is that the seat 46" now crosses the line of separation of the instrument guide 12 and guide 40 thereby risking leakage between these two parts even when the ball closes the seat 46".

Figure 13:
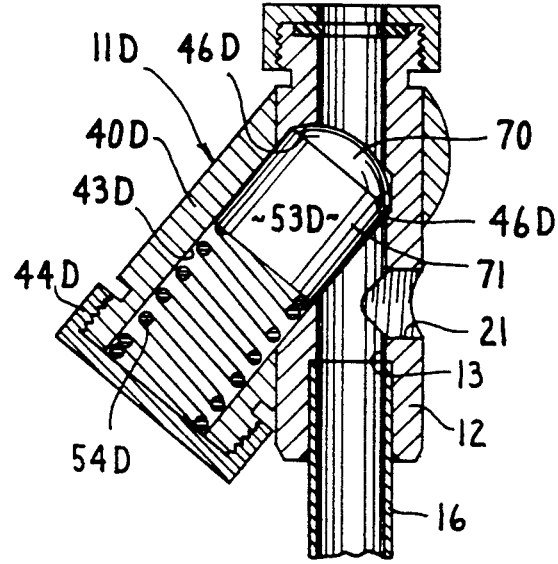
FIG. 13 is a view similar to FIG. 4A and showing a modification.

FIG. 13 shows a further modification in which the valve member 53D is modified in shape. More particularly, the valve member 53D could be thought of as the top front 20% or so of the FIG. 4A ball 53 with a cylindrical downward and rearward extension. The spherical and cylindrical parts of the valve member 53D are indicated at 70 and 71. The overall length of the valve member 53D may be approximately equal to the diameter of the ball 53 of FIG. 4A. The resulting round-nosed, cylindrical valve member 53D is advantageous in that it permits the passage 43D, tubular guide 40D, cap 44D and spring 54D to be reduced somewhat in diameter, making the FIG. 13 apparatus more compact. Also, even with a strictly cylindrical spring 54D, the modified FIG. 13 construction does not expose any portion of the spring to the instrument passage even when the valve member is fully closed against its seat as in FIG. 13. The cylinder-like valve member 53D cannot pivot in pitch and yaw, unlike the FIG. 4A ball 53. Thus, the modified valve member 53D normally responds to insertion of an instrument downwardly therepast by simply translating downward and rearward along the valve guide 40D against the spring 54D.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. Apparatus for laparoscopic, arthroscopic and similar surgery and particularly for guiding therethrough the sequential insertion of a series of differing surgical instruments into a surgical site, while blocking escape therethrough, from the surgical site, of surgical site ballooning, namely surgical chamber creating gas under pressure, the apparatus comprising:

(a) means for sequentially guiding therethrough of a series of differing elongate surgical instruments into, and then out of, a pressure gas inflated surgical site, said means defining an elongate instrument guide, said instrument guide having a distal end insertable in the surgical site and a near end opposite said distal end, said instrument guide containing an elongate cylindrical instrument passage for radially snugly guiding therethrough in sequence a series of differing elongate surgical instruments into and out from the surgical site;

(b) a valve seat in said instrument passage;

(c) means for blocking escape of gas under pressure from the surgical site therepast along said instrument passage when no instrument occupies said instrument passage and means comprising a ball movable into contact with said valve seat;

(d) a ball guide having elongate ball guide passage means for guiding said ball along the length axis of said ball guide passage means toward and away from said instrument passage, said ball guide passage means comprising an elongate ball guide passage having a perimeter wall means for snugly constraining said ball against movement away from said length axis but allowing free translation of said ball along said length axis while permitting rotation of said ball about three mutually orthogonal axes, namely in pitch and roll and yaw, said elongate ball guide passage intersecting said instrument passage;

(e) resilient means backing said ball (1) for pushing said ball along the length axis of said ball guide passage into said instrument guide passage and against said valve seat to close said instrument passage when no surgical instrument is in said instrument passage and (2) for resiliently allowing a surgical instrument, moving along said instrument passage toward the surgical site, to push said ball back into said ball guide passage, said resilient means defining a coil compression spring in said ball guide passage, said ball normally engaging said valve seat in said instrument passage but having surface means responsive to pressure thereon by an instrument in said instrument passage for translating said ball back along said ball guide passage against said spring and out of said instrument passage in which said spring is always fully hidden outside of said instrument passage and in said ball guide passage by said ball even with said ball fully seated against the valve seat;

(f) a substantially Y-shaped housing defining said ball guide passage and a central portion of said instrument passage communicating with said ball guide passage;

(g) means for avoiding unintended locking in said instrument passage, by said ball, of an instrument having a central portion adjacent said ball and a relatively larger cross section distal portion between the ball and the surgical site to form a step axially facing the ball and away from the surgical site, said lock avoiding means including:

(1) intersection of the respective length axes of said ball guide passage and instrument passage an angle in the range of 30° to 45° and opening toward the distal end of the instrument guide, wherein an instrument extending in said instrument passage past the ball would abut the ball at a point on the ball spaced between said valve seat and an imaginary diametral plane through the center of said ball and perpendicular to the length axis of said ball guide passage, and (2) the valve seat being located so that, with the ball occupying the valve seat (i) the center of the ball is spaced radially slightly outside of the instrument passage and in a direction such that movement of said ball away from said valve seat to open said valve seat moves the ball further away from said instrument passage and (ii) the center of said ball cannot enter said instrument passage, the diameter of said ball slightly exceeding the twice the diameter of said instrument passage, such that such a step in the instrument can contact the ball near said diametral plane of the ball, which diametral plane is perpendicular to the ball guide passage length axis seal means for sealing around an instrument during insertion and removal thereof from said instrument passage, said ball guide passage intersects said instrument passage at a location axial between said distal end of said instrument passage and said seal means.

2. The apparatus of claim 1 which said angle is about 40°.

3. The apparatus of claim 1 including a gas stopcock mounted on and communicating through the sidewall of said Y-shaped housing and with said instrument passage at a location between said valve seat and the surgical site end of said instrument passage, for applying pressure gas to the surgical site.

4. The apparatus of claim 1, in which said housing comprises a ball guide in which said ball guide passage extends said ball guide having a through hole for snugly and sealingly and fixedly receiving therethrough the central portion of an instrument tube defining said instrument passage.

* * * * *

UNITED STATES PATENT AND TRADEMARK OFFICE
CERTIFICATE OF CORRECTION

PATENT NO. : 5,261,895

DATED : November 16, 1993

INVENTOR(S) : Joseph J. KABLIK

It is certified that error appears in the above-identified patent and that said Letters Patent is hereby corrected as shown below:

Column 12, line 8, "axial" should read --axially--

Signed and Sealed this

Twenty-fourth Day of May, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,261,895
DATED : November 16, 1993
INVENTOR(S) : Joseph J. Kablik

It is certified that error appears in the above-indentified patent and that said Letters Patent is hereby corrected as shown below:

Column 10, line 26; change "and" to ---said escape blocking---.

Signed and Sealed this

Seventh Day of February, 1995

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,261,895
DATED : November 16, 1993
INVENTOR(S) : Joseph J. Kablik

It is certified that error appears in the above-indentified patent and that said Letters Patent is hereby corrected as shown below:

Column 12, line 19; change "a" to ---said---.
         line 20; after "extends" insert ---,---.

Signed and Sealed this

Tenth Day of December, 1996

Attest:

BRUCE LEHMAN

*Attesting Officer*     *Commissioner of Patents and Trademarks*